United States Patent
Wilhelm

(10) Patent No.: US 9,260,243 B2
(45) Date of Patent: Feb. 16, 2016

(54) DEVICE AND METHOD FOR STORING AND ORDERING BIOLOGICAL SAMPLING BLOCKS

(71) Applicant: DREAMPATH DIAGNOSTICS, Strasbourg (FR)

(72) Inventor: Valerie Wilhelm, Illkirch-Graffenstaden (FR)

(73) Assignee: DREAMPATH DIAGNOSTICS, Strasbourg (FR)

( * ) Notice: Subject to any disclaimer, the term of this patent is extended or adjusted under 35 U.S.C. 154(b) by 0 days.

(21) Appl. No.: 14/371,435

(22) PCT Filed: Jan. 9, 2013

(86) PCT No.: PCT/FR2013/050052
§ 371 (c)(1),
(2) Date: Jul. 9, 2014

(87) PCT Pub. No.: WO2013/104865
PCT Pub. Date: Jul. 18, 2013

(65) Prior Publication Data
US 2014/0330427 A1    Nov. 6, 2014

(30) Foreign Application Priority Data

Jan. 10, 2012  (FR) ...................................... 12 50244

(51) Int. Cl.
| G06F 19/00 | (2011.01) |
| B65G 1/137 | (2006.01) |
| G07F 11/62 | (2006.01) |
| G07F 17/00 | (2006.01) |
| A61B 10/00 | (2006.01) |

(52) U.S. Cl.
CPC ............ *B65G 1/137* (2013.01); *A61B 10/0096* (2013.01); *G07F 11/62* (2013.01); *G07F 17/0092* (2013.01)

(58) Field of Classification Search
CPC ........................................................ G07F 11/62
USPC ........................................................... 235/385
See application file for complete search history.

(56) References Cited

U.S. PATENT DOCUMENTS

| 8,770,479 B1 * | 7/2014 | Shoenfeld ..................... 235/385 |
| 2001/0032035 A1 | 10/2001 | Holmes et al. |
| 2007/0135965 A1 | 6/2007 | Nguyen et al. |

FOREIGN PATENT DOCUMENTS

| EP | 0706825 A1 | 4/1996 |
| WO | 9960982 A2 | 12/1999 |
| WO | 2005054992 A2 | 6/2005 |
| WO | 2010004331 A1 | 1/2010 |

* cited by examiner

Primary Examiner — Jamara Franklin
(74) Attorney, Agent, or Firm — Andrew W. Chu; Craft Chu PLLC

(57) ABSTRACT

The device for storing and ordering biological sampling blocks, each block being in the form of a housing provided with identification information on one surface thereof, includes: storage for at least one element as a horizontally-extending drawer for positioning the blocks vertically in columns and rows with the above-mentioned surface facing upward, and with a nesting device provided as regularly spaced projections or recesses, forming male and female parts on the base, in which the blocks can be inserted; and a device for referencing the position of each block within the storage. The device for referencing includes a device for reading the identification information of each block and for the computerized recording of the position. The method includes using this device.

5 Claims, 1 Drawing Sheet

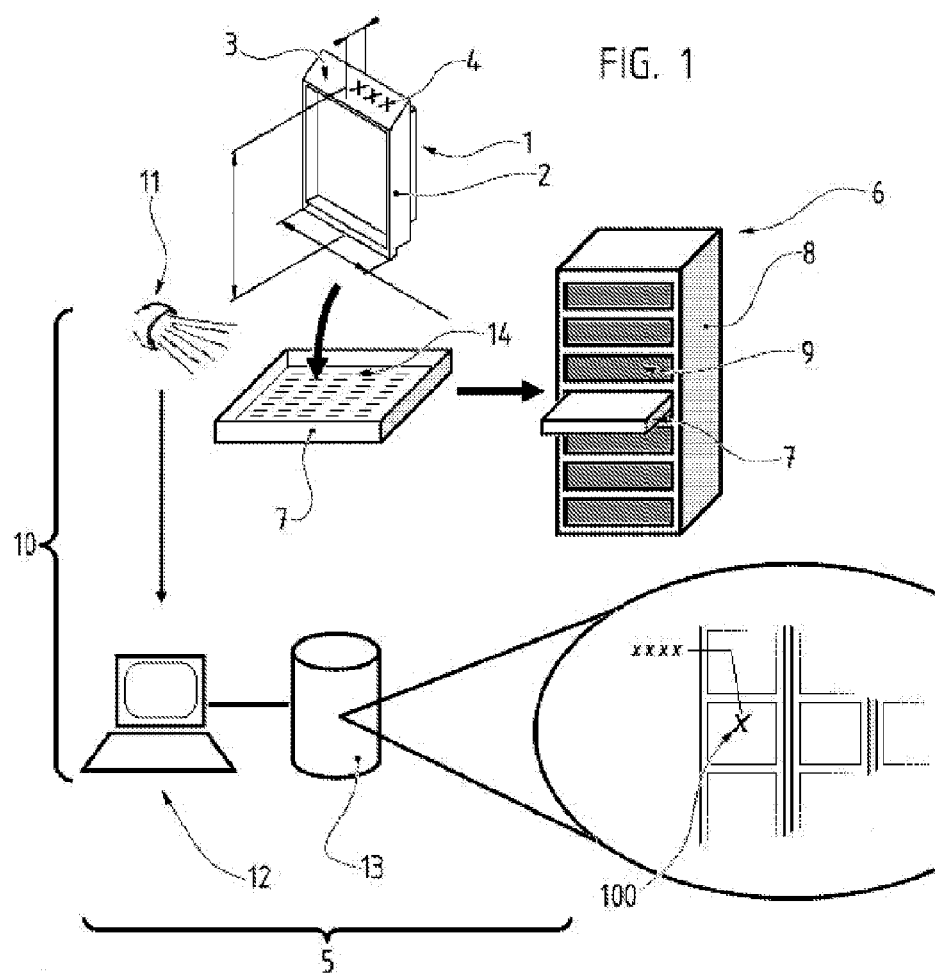
FIG. 1
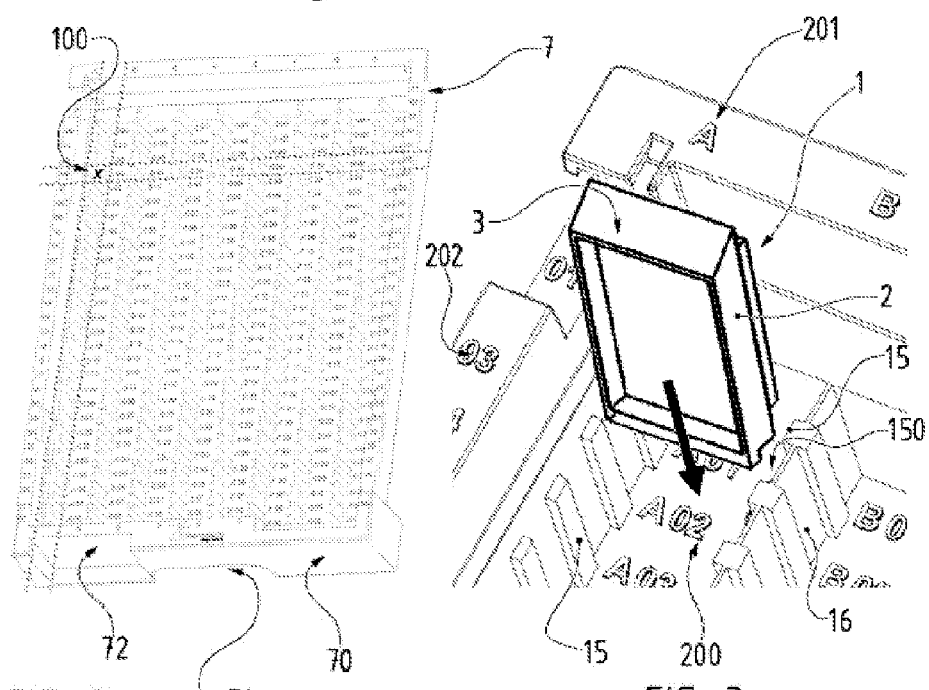
FIG. 2
FIG. 3

DEVICE AND METHOD FOR STORING AND ORDERING BIOLOGICAL SAMPLING BLOCKS

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention falls within the medical field of analysis of tissue and cell samples.

The invention relates in particular to the preservation and storage of such samples.

Within the framework of the medical care of a patient or within the framework of the research, the cell or tissue sampling may be performed for a histological and/or molecular analysis. For preservation purposes, these elements are dehydrated and then stored embedded in paraffin in a support, commonly referred to as "paraffin blocks". After carrying out the cuts necessary for the histological and/or molecular analysis, the tissue and cell residues embedded in paraffin are stored in order to permit to accede later on to complementary analyses (sometimes years later).

2. Description of Related Art Including Information Disclosed Under 37 CFR 1.97 and 37 CFR 1.98.

Such paraffin blocks are generally formed of a housing made of plastic material having a standard shape, a rectangular parallelepiped shape, the bottom of which is pierced with through-orifices. In addition, one of the sidewalls, generally the front wall, receives unique identification information for the sample, such as a reference. Such a wall may be designed inclined, in order to facilitate the reading of said information.

Several examples of such housings are described in U.S. D448 487 S, U.S. Pat. No. 4,421,246 and GB 2,113,249. Generically, these housings are referred to as "cassettes".

A detail of FIG. 1 shows a perspective view of an exemplary housing or cassette in vertical position, the upper face facing forward. Such a cassette has a height of 41.8 millimeters (mm), for a width of 28.5 mm and a height or thickness of 6.5 mm.

Thus, in such a cassette is deposited the biological sample and it is provisionally closed by a removable cover, which is then removed at the time of embedding into paraffin, the upper face revealing the paraffin, which can subsequently be taken out with the sample it encloses. The cassette and the sampling embedded in paraffin constitute then a paraffin block.

These blocks and the sample preserved in same are listed and stored by various institutions, namely medical analysis laboratories. Legally, their storage is compulsory for each person over a minimum period of ten years for a private company, up to several decades for a public institution or a pharmaceutical industry.

At present, said blocks are ordered and handled manually by operators, who necessarily received no specific training, without any control. Therefore, such a manual management gives rise to errors and a considerable loss of time in their search, up to the detrimental loss of some samples.

Moreover, in this context the quantities of existing blocks are constantly evolving: from about 200 million per year in the 1990's, their number has increased to nearly 400 million per year in 2010 and this growth is estimated at 750 million per year by 2030. Therefore, the storage capacities and the empirical means presently implemented are not designed to support the management of a rational and safe storage for such quantities.

At present, there is no appropriate solution dedicated to the storage and management of such blocks. It should however be noted that other systems for managing medical equipment exist, without therefore being adapted.

US 2007/135965 describes a device for storing medical objects, providing management of the traceability of their use. Such a device is in the form of a cupboard provided with trays or drawers, divided internally into compartments by vertically protruding walls. In particular, these compartments have dimensions that can be adapted by moving said walls, in order to change their respective size depending on the size of the objects they are aimed at receiving.

In addition, this device integrates data-processing means for managing the access to each compartment. In particular, these means permit to read a code on each object and to reference the information related to same. In addition, these management means permit to quickly and easily find, by means of a touch interface providing an accurate graphical display, the compartment in which the object looked for is located.

Another solution is described in WO 99/60982 relating to a housing device with a hinged cover, aimed at receiving drugs in same. In particular, such a housing can be positioned in a drawer provided for this purpose. During their ordering, several housings are positioned side by side in columns and rows. Moreover, a protruding label on the lower face of the bottom of each housing is aimed at cooperating by snapping into a slot provided for in the upper face of the bottom of said drawer. Each housing also comprises internally electronic identification means, which, during their nesting within the drawer, permit to establish a connection and to accurately identify the position of each housing in the drawer.

Yet another solution is described in document US 2001/032035 relating to a tray aimed at being placed in a drawer. Said tray comprises removable inner walls, so as to divide their interior into several compartments, the dimensions of which are adaptable depending on the objects they will receive.

Such systems are thus clearly not adapted to the management of items that are all identical and of small dimensions, such as the paraffin blocks. In addition, the systems of the state of the art do not provide for any particular positioning of the objects, all different and of heterogeneous shapes, they intend to store without taking into consideration the peculiarities of each of them.

In addition, it should be noted that known technologies are implemented to facilitate the identification and the traceability of objects in the medical field. By way of an example, the RFID (for "Radio Frequency Identification") technology can be used through contiguous chips attached to such objects, ensuring their automatic identification through a wireless reader having a short-range detection field ("Near Field Communication"). Since the reader is connected to a remote data-processing manager, it permits to perform a tracking of the objects used and to manage their supply. An example of such a solution is contemplated through WO 2005/032035.

A similar solution consists in providing a sampling-pipe support, such as a test tube, with a data-processing memory in which can be stored information related to said sampling. It is then no longer necessary to apply the information directly on the sampling tube. An example of such a solution is described in EP 0 706 825.

However, these solutions provide a technology for containing information relating to objects, without therefore ensuring their classification and ordering, in particular for large quantities of identical objects.

SUMMARY OF THE INVENTION

The present invention is aimed at coping with the drawbacks of the state of the art by providing a computerized and automated system for ordering biological sampling blocks. Such a system pretends to be capable of providing a traceability and a rational management of blocks, for large quantities, namely distributed into different geographical locations.

To this end, such a system first of all provides for means for storing several blocks, through positioning within at least one horizontal storage compartment, in columns and rows, so as to be arranged vertically, the front face including identification information facing upwards. In addition, the invention does not use any ordering at the level of such a storage, the blocks being positioned in no particular order of arrangement during the filling of the columns and rows.

In particular, the nature of the ordering results from this particular storage through automatic means for reading said information present on each block and the computerized referencing of the position of said block in the storage means.

Thus, the present invention relates in the first place to a device for storing and ordering biological sampling blocks, said blocks being in the form of a housing provided on one surface with identification information. Such a device is characterized in that it comprises, on the one hand, means for storing formed of at least one element in the form of a horizontally-extending drawer for positioning said blocks vertically in columns and rows, said surface facing upward, through nesting means provided in the form of regularly spaced projections or recesses, thus forming male and female parts at the level of the bottom, in which the blocks can be inserted and, on the other hand, means for referencing the position of each block within the storing means, said referencing means comprising means for reading the identification information of each block and for the computerized recording of said position.

In addition, according to other features, said recesses can be formed protruding along and on both sides of the vertical inner walls, oriented so as to define columns.

Preferably, said storage means can comprise at least one cupboard for storing several elements, which is then in the form of drawers.

According to one embodiment, said referencing means can comprise computerized means for searching said position of a block based on its identification information.

In particular, said reading means can comprise a reader such as a light scanner for encoded data, namely such as bar code or matrix code.

The invention also relates to a method for storing and ordering biological sampling blocks, said blocks being in the form of a housing provided on one face with identification information, wherein:

at least one block is positioned vertically, in columns and rows, said face facing upwards, within a horizontally extending storage element, such as a drawer, provided with nesting means arranged in the form of regularly spaced projections or recesses, thereby providing male and female parts at the level of the bottom, forming spaces in which said blocks can be inserted; and a referencing of the position of said block in said storage element is carried out by reading said identification information and computerized recording of their position.

Therefore, the invention ensures a storage specifically adapted and in conformity with the size of said blocks, dimensioned accordingly. This dedicated storage thus permits to store a large number of blocks, while knowing exactly their location.

In this respect, the positioning of the blocks pretends to be arbitrary, so that an operator can place them without worrying about a predetermined location or order, which decreases the time required for a classification that is carried out by automatically identifying each block and its location.

Thus, the invention can quickly and easily store, without any need for special training of the operator, a large number of blocks that will automatically be classified and located through a data-processing tool, ensuring their full traceability.

Other features and advantages of the invention will become clear from the following detailed description of non-restrictive embodiments of the invention, with reference to the attached figures.

BRIEF DESCRIPTION OF THE DRAWINGS

FIG. 1 schematically shows the architecture of the storage and ordering system according to the invention.

FIG. 2 shows a perspective view of a storage element such as a drawer according to a preferred embodiment.

FIG. 3 shows a schematic view of a detail of FIG. 2, showing a block during its vertical insertion, the front face facing upwards, in a position of said drawer.

DETAILED DESCRIPTION OF THE DRAWINGS

The present invention relates to the storage and ordering of biological sampling blocks 1.

It should be noted that such blocks 1 serve as a support for the preservation of biological samples, such as tissues or cells. They are in the form of a housing 2, namely shaped as a rectangular parallelepiped, provided on one face with identification information, namely at the level of the outer wall of the front face 3 of the block 1. This front face 3 is in fact often designed inclined, in order to facilitate the reading of said information, when the block 1 is placed at the level of its bottom.

The latter permits to identify in a unique way the person to whom this sampling belongs, as well as other related information, such as for example, in a non-restrictive way, the date and type of sampling or the analyses on one or several samples of this sampling.

It should be noted that this information can be printed on each block 1 in the form of encoded data. The latter can be applied at the time of their manufacture and correspond then to a unique number for each block 1.

By way of an example, said data can be in the form of an encoding such as a bar code or matrix code 4, which can be read by a suitable scanner, namely a light scanner.

In addition, said unique number can be matched, when placing the sample within its block 1, with said identification information. This matching can be done by assigning the unique number in a person-specific medical computer file, in the field of health, but also of research.

Advantageously, in a first step, the present invention relates to a device 5 for storing and ordering such blocks 1. This device 5 pretends to be able to be completely dedicated to this management of blocks 1, which are all identical, thus facilitating their storage as well as their classification, in order to quickly and easily find the location of each of them, regardless of their number.

To this end, on the one hand, said device 5 comprises storage means 6 formed of at least one element 7 for positioning said blocks 1 in columns and rows.

In particular, such an element 7 extends horizontally and permits the positioning of said blocks 1 vertically, said face 3 facing upwards. Thus, it is possible to read, visually or automatically by a suitable system, the identification information of each block 1 when it is stored in an element 7 of the device 5.

According to the preferred embodiment, said storage means 6 can comprise at least one storage cupboard 8 with several elements 7 that are then in the form of drawers. The latter are then superimposed and/or juxtaposed. In particular, several drawers can be slidably mounted in corresponding recesses 9 provided for in said cupboard 8, in columns, rows, or both.

According to the exemplary embodiment shown in FIG. 1, such a cupboard 8 can be in the form of a vertical unit comprising the recesses 9 for receiving seven drawers. Such a cupboard can however be dimensioned to receive more or less drawers, in more than one column.

In addition, each cupboard 8 can provide for hermetic closing means, such as doors, permitting to ensure that the interior of said cupboard 8 is maintained under a particular, namely refrigerated or depressurized atmosphere or under a specific gas. This peculiarity ensures a better preservation of the so stored samples.

It should be noted that each cupboard 8 and each drawer element 7 can receive unique identification information, such as a serial number, permitting to uniquely identify them, so as to be matched with each other, i.e. several drawers 7 can be associated with a cupboard 8, namely at its recesses 9 or at one of its recesses 9 in particular.

In the latter case, said recesses 9 can comprise means slidably receiving each drawer 7, in the form of guiding tabs, having complementary receiving means at the level of said drawer 7, ensuring that a drawer 7 is correctly positioned within the recess 9 that is intended for same.

Such guiding tabs be in the form of a particular slide, guiding groove, groove equipping said drawer 7 at the level of its outer walls, in particular its sidewalls. These guiding tabs can then be a male or female part aimed at cooperating reciprocally with a female or male part formed in each recess 9.

Furthermore, according to the preferred embodiment, as shown in the figures, said device 5 comprises elements 7 in the form of drawers. In order to permit the vertical positioning of the blocks 1, facilitating their identification once in place, each drawer 7 has, at the level of its bottom, nesting means 14. The latter are provided in the form of evenly spaced projections or recesses 15, thus providing male and female parts at the level of said bottom, into which said blocks 1 can be inserted. In brief, the space between each projection or recess 15 constitutes a housing or a slot 150 for receiving the nesting of a block 1.

According to the embodiment shown in FIG. 3, said recesses 15 are formed projecting at the level of the bottom, namely in the lower portion of the drawer, but along and on both sides of vertical inner walls 16. The latter are oriented parallel to each other, at regular intervals, so as to define columns within said element 7, namely said drawer.

It should be noted that the spacing between the projections or recesses 15 is dimensioned so as to permit the nesting of each block 1, with or without backlash, preferably without backlash. In the latter case, the width of each spacing, i.e. the distance between the surfaces of two consecutive projections or recesses 15, is almost equal to the thickness of a block 1, within one to several tenths of a millimeter. Thus, once it has been nested, each block 1 is held in its position, even if the drawer happens to be turned upside down.

Thus, the spacing between the projections substantially corresponds to the thickness of a block 1, so as to ensure its nesting without backlash or with a minimum backlash, said block 1 then being nested by force and held, even in the event the drawer 7 is turned upside down.

According to the example of paraffin blocks mentioned in the introductory part, the width of a row can be of about 29 millimeters (mm), preferably of 29.2 mm for a block of a width of 28.5 mm. The spacing between the projections or recesses 15 may then be of about 6 mm, preferably of 6.6 mm, for a block of a thickness of 6.6 mm. Finally, the height of the drawer can be of about 50-60 mm, preferably of 53.5 mm, for a block length of 41.8 mm, while the height of the middle wall 16 can be smaller, namely of at least 10 to 30 mm, thus letting protrude the top of the blocks 1, permitting to facilitate their gripping.

In addition, the thickness of said projections, lugs or recesses 15 permits the automatic or manual, namely robotized gripping and extraction, of the blocks 1. To this end, according to a particular embodiment, said projections or recesses 15 can extend only over part of the height of each median inner wall 16. Preferably, the upper portion of each wall 16 is without recesses 15, the latter extending only from the bottom over a height of less than that of the sidewalls, which surround it, namely the two walls 16 or the side edges of said element 7.

In addition, according to a preferred embodiment, each drawer can receive on the open upper face a removable cover, which permits to close the drawer, namely with a view to its handling. It should be noted that the backlash between the lower face of said cover and the blocks 1 positioned in the drawer 7 is such that said blocks 1 cannot change their position. In brief, this space does not permit that a block 1 completely leaves it recess when the drawer is turned upside down.

According to another embodiment, the upper and lower faces of each drawer 7 can mutually receive nesting and complementary nesting means, shaped so as to permit their superimposition while maintaining them on top of each other. In brief, the nesting means can consist of male parts that insert into female parts formed by said complementary means, or vice-versa. It is thus possible to stack several drawers 7.

Therefore, when several drawers are stacked 7, only the upper drawer can be closed by said cover.

According to the preferred embodiment, each drawer 7 can comprise a space 72 reserved for data ensuring its identification in a unique way. These data can be of any type, namely encoded so as to be read by light scanners, of the bar code reader or similar type. These data can also be detected through wireless means, namely through a RFID (for "Radio Frequency Identification") technology.

In addition, said reserved space 72 can be provided at the level of one of the edges of the drawer 7, namely located at the level of its front face 70, in the form of a bevel on which said identification data are printed. This bevel provides an inclined surface the orientation of which facilitates the reading of said data, manually or automatically.

According to the embodiment of FIG. 2, the drawer 7 can comprise, on the front face, gripping means 70 in the form of a handle 71, namely provided for in the wall by a reserved space. This handle 71 permits to insert and extract the drawer 7 from the cupboard 8, but also to carry it as a suitcase, when closed by the cover.

On the other hand, said device 5 comprises means 10 for referencing the position 100 of each block 1 within said storage means 6. Such referencing means 10 comprise means 11 for reading the identification information, in particular encoded data 4, of each block 1 and computerized recording of said position 100 of each block 1.

In brief, once the block 1 is positioned within the drawer 7, the reading means 11 record its exact position 100, namely using two-dimensional two-digit coordinates, depending on the rows and columns corresponding to the abscissae and ordinates, respectively. A column and a row have been shown schematically in dotted line in FIG. 2, where the intersection constitutes a position. In addition, the data of said drawer 7 can be added, by way of additional coordinates, said drawer 7 being then aimed at being inserted into a cupboard 8, the identification of which can also be added. This provides a system for referencing the position of each block 1 varying from two to four dimensions.

Therefore, it is possible to know, for each block 1, its exact position 100 depending on the coordinates related to the different identification data of the different parts of the device 5 according to the invention. It should be noted that this position 100 can then be stored in a digital data base 13, provided with a manager, in order to facilitate its subsequent access.

Conversely, once this position 100 has been recorded, the device 5 permits to find it. To this end, said referencing means 10 comprise computerized means 12 for searching said position 100 of a block 1 based on its identification information. These searching means 12 can be in the form of a computer terminal provided with manual or automatic input means, namely by means of said reading means 11. In brief, an operator can input a code, an identification number or scan a label on which the data of a block 1 are printed, and the searching means 12 interrogate said database 13, in order to retrieve the position 100 and locate said block 1 within the device 5.

Then, the operator only has to open the corresponding drawer and locate said position. In this respect, each drawer 7 can comprise, at the level of the upper faces of its various walls (such as the bottom, the peripheral edges or the upper edges of the vertical walls) digital data 200 identifying each row and column. In particular, according to the preferred embodiment visible in FIGS. 2 and 3, letters 201 can identify the columns, while numbers can identify the rows 202. Thus, the highest and leftmost position, located in the upper left corner, has the position A01, the position immediately to the right B01, while the position immediately below A02.

In addition, on the upper face of the bottom of the drawer 7, namely internally, at the level of each housing 150, can be found said position 200 (A01, B01, A02, . . . ) provided for in projection or recess. In addition, this position number can be located between the projections or recesses 15, permitting a user to more easily visualize it, even when a block 1 is inserted therein.

In addition, in the case of a drawer 7 made of plastic material, these numbers and letters are molded directly during the manufacture, preventing any subsequent modification.

According to an additional feature, the invention permits to verify the presence or absence of a block 1 in each position of the drawer. Based on this verification of the positions, comparisons can be contemplated with the already known positions, in order to verify the incorrect placement, the moving or removing of a block 1. In case a difference is observed, an alarm can be issued in order to inform an operator of same.

It should be noted that, according to a particular embodiment, digital photographic images of each block can be taken automatically during their positioning. These pictures permit to facilitate the subsequent identification of the block, namely because of its color, but will also ensure a manual input of an identification of a block 1 after an incorrect reading, but also the input of its identification if the latter was not provided with an identification in the form of encoded data 4. This image will also serve as a proof of the physical presence of these blocks 1 for traceability purposes and/or to storage outside the premises of the laboratory, hospital or academic or private research centers.

It should be noted that, according to a preferred embodiment, said reading means 11 comprise a reader such as a light scanner for encoded data 4, namely of the type single- or two-dimensional bar code or matrix code. Such a reader can be used and manipulated manually, or automatically.

In the latter case, the invention can provide for performing an automatic reading of all the data 4 of each block 1 stored in a drawer, as soon as the latter is placed at the level of the reading means 11.

In this respect, the latter can be integrated into each cupboard and a reading of each drawer is performed when the latter is replaced, after a previous extraction, or closed, if it had been opened.

Thus, the reading can permit to detect any change of place, addition or removal of a block, with respect to the previous classification, already known and stored, through a simple comparison.

According to another embodiment, said reading means 11 can use wireless technologies, namely of the RFID type.

In addition, said searching means 12 permit to follow up the handling of a block 1. In brief, a traceability is possible in an automatic and transparent way for the user, permitting to know whether it is stored in the device 5 or it has been removed, by which person, and to thus follow its path.

In addition, during its return to the device 5, the positioning of the block 1 can occur at a different place, arbitrarily chosen by the operator, and the system updates said position 100 automatically, through a reading step. It is then possible to position the blocks 1 without worrying about a specific order, but maintaining with certainty the exact location in order to find them. In brief, an operator can position a block 1 in any free location, thus accelerating the storage in the case of several blocks.

Therefore, it is possible to contemplate a comprehensive monitoring of the entire system, of the devices 5 installed and the positions of all the existing blocks 1, permitting to locate them geographically.

The invention also relates to a method for storing and ordering blocks 1 of biological samples, said blocks 1 being in the form of a housing 2 provided, on one face 3, with identification information, wherein:

at least one block 1 is positioned vertically, in columns and rows, said face 3 facing upwards, within a horizontally extending storage element 7, such as a drawer, provided with nesting means arranged in the form of regularly spaced projections or recesses 15, thereby providing male and female parts at the level of the bottom, forming spaces in which said blocks 1 can be inserted; and a referencing of the position 100 of said block 1 in said storage element 7 is carried out by reading said identification information and computerized recording of their position 100.

As mentioned above, the positioning of each block 1 can be performed arbitrarily within the spaces of the nesting means.

Thus, the present invention permits to quickly and easily store blocks 1, to keep them in this ordered state, while ensuring a traceability of the samples contained therein.

In addition, the invention permits to be adapted to storage solutions existing in laboratories, hospitals, private and academic research centers, but can also be transposed to a different center for total and rationalized outsourcing of the storage and referencing of the blocks.

I claim:

1. A device for storing and ordering, comprising:
    a plurality of biological sampling blocks, wherein each block is comprised of a housing having one surface with identification information, said identification information being comprised of encoded data, each block being identical in shape to another block; and
    means for storing being comprised of a horizontally extending drawer, each block being positioned vertically in columns and rows with each respective one surface facing upward, the drawer having a bottom with a nesting means and side walls, said nesting means being comprised of vertical inner walls with regularly spaced projections and recesses so as to form female parts on said bottom, wherein the regularly spaced projections and recesses are set relative to said side walls of the drawer, wherein each female part has a set position in the drawer relative to said side walls and said vertical inner walls, and wherein each block is insertable in any female part and a respective set position in the drawer; and
    means for referencing position of each block within the drawer, wherein said means for referencing comprise means for automatically reading said identification information and for computerized recording and automatic updating of a respective set position within the drawer of respective identification information for each block, said means for reading comprising a reader for encoded data.

2. Device according to claim 1, wherein said vertical inner walls have said projections and said recesses along and on both sides, wherein said female parts are formed on both sides of said vertical inner walls, said female parts being aligned in columns.

3. Device according to claim 1, wherein said means for storing further comprises:
    at least one storage cupboard, the drawer being mounted in the storage cupboard; and
    another drawer having another bottom with another nesting means, wherein another set of blocks are inserted in corresponding female parts in said another drawer.

4. Device according to claim 1, wherein said means for referencing comprise computerized means for searching a set position of a block based on identification information.

5. Method for storing and ordering, said method comprising the steps of:
    assembling a device comprising:
        a plurality of biological sampling blocks, wherein each block is comprised of a housing having one surface with identification information, said identification information being comprised of encoded data, each block being identical in shape to another block; and
        means for storing being comprised of a horizontally extending drawer, each block being positioned vertically in columns and rows with each respective one surface facing upward, the drawer having a bottom with a nesting means and side walls, said nesting means being comprised of vertical inner walls with regularly spaced projections and recesses so as to form female parts on said bottom, wherein the regularly spaced projections and recesses are set relative to said side walls of the drawer, wherein each female part has a set position in the drawer relative to said side walls and said vertical inner walls, and wherein each block is insertable in any female part and a respective set position in the drawer; and
        means for referencing position of each block within the drawer, wherein said means for referencing comprise means for automatically reading said identification information and for computerized recording and automatic updating of a respective set position within the drawer of respective identification information for each block, said means for reading comprising a reader for encoded data;
    loading said plurality of sampling blocks with biological samples, said identification information being associated with a respective block and a respective biological sample in said respective block;
    positioning each block in a female part of said nesting means on said bottom of the drawer, each block being oriented vertically with each respective one surface facing upwards, each female part having a set position corresponding to columns and rows formed by said side walls of the drawer and said vertical inner walls of said nesting means;
    associating said identification information of each block with a corresponding set position, each set position determined by said projections and said recesses of said vertical inner walls of said nesting means; and
    referencing said corresponding set position of each block by automatic reading said identification information by a reader, each set position and associated identification information being computer recorded and automatically updated.

* * * * *